United States Patent [19]

Greenleaf et al.

[11] 4,190,060
[45] Feb. 26, 1980

[54] SWEAT COLLECTION CAPSULE

[75] Inventors: John E. Greenleaf, Sunnyvale; Robert W. Delaplaine, Woodside, both of Calif.

[73] Assignee: The United States of America as represented by the Administrator of the National Aeronautics and Space Administration, Washington, D.C.

[21] Appl. No.: 897,828

[22] Filed: Apr. 19, 1978

[51] Int. Cl.² .............................................. A61B 10/00
[52] U.S. Cl. .................................... 128/760; 128/275
[58] Field of Search .............. 128/2 F, 280, 2 E, 2 H, 128/2 W, 2 R, 293, 172.1, DIG. 15

[56] References Cited

U.S. PATENT DOCUMENTS

| | | | |
|---|---|---|---|
| 2,924,219 | 2/1960 | Wershaw | 128/260 |
| 3,289,671 | 12/1966 | Troutman | 128/172.1 |
| 4,026,290 | 5/1977 | Brooker et al. | 128/260 |
| 4,036,229 | 7/1977 | Marinello | 128/268 |

FOREIGN PATENT DOCUMENTS

| | | | |
|---|---|---|---|
| 195034 | 6/1967 | U.S.S.R. | 128/2 R |
| 249546 | 12/1969 | U.S.S.R. | 128/2 R |

*Primary Examiner*—Robert W. Michell
*Assistant Examiner*—J. L. Kruter
*Attorney, Agent, or Firm*—Armand McMillan; John R. Manning; Darrell G. Brekke

[57] ABSTRACT

Sweat collection capsule permitting quantitative collection of sweat, comprising a frame held immobile on the skin, a closure secured to the frame and absorbent material located next to the skin in a cavity formed by the frame and the closure. The absorbent material may be removed from the device by removing the closure from the frame while the frame is held immobile on the skin.

4 Claims, 3 Drawing Figures

SWEAT COLLECTION CAPSULE

ORIGIN

The invention described herein was made by employees of the United States Government and may be manufactured and used by or for the Government for governmental purposes without the payment of any royalties thereon or therefor.

THE PRIOR ART

Human sweat collection has been of interest in several diverse contexts. The athlete is served by a device which permits an absorbent towel to be affixed to his arm. The towel is thus immediately available to absorb sweat generated during a game (British Pat. No. 476,063). The interests of the over-weight person may be aided by an airtight elastic material which is wound around the body allegedly preventing evaporation of sweat and causing weight reduction.

Where the end objective in the sweat collecting process is quantitative recovery of the sweat, it has been taught that a device which prevents evaporation of the sweat and provides a means for absorbing the sweat is required (U.S. Pat. No. 3,289,671). The prior art method suggests satisfying these requirements by securing an inverted watch glass containing an absorbent material over the area of skin from which the sweat is to be collected.

The shortcoming of this prior art method of quantitative sweat collection is that the watch glass must be lifted from the skin, at least in part, in order to allow recovery of the absorbent material contained thereunder. When one is interested in repeated recoveries and replacements of the absorbent material used to collect the sweat, this method is unsatisfactory since error may be introduced through movement of the watch glass.

The present invention provides an improved device to be used in the quantitative collection of human sweat.

SUMMARY OF THE INVENTION

The sweat collecting capsule of the present invention consists essentially of a frame which is held immobile on the surface of the skin and a removable closure which is secured to the frame in an airtight manner. An abosrbent material is located next to the skin in a cavity created by the frame and the closure. The improvement in sweat collecting that this invention teaches is that the absorbent material may be recovered by removing the closure of the capsule from the frame while the frame remains in place on the skin.

DETAILED DESCRIPTION

The present invention, along with its method of use, can be best understood by referring to the accompany drawings in which.

Figure 1:
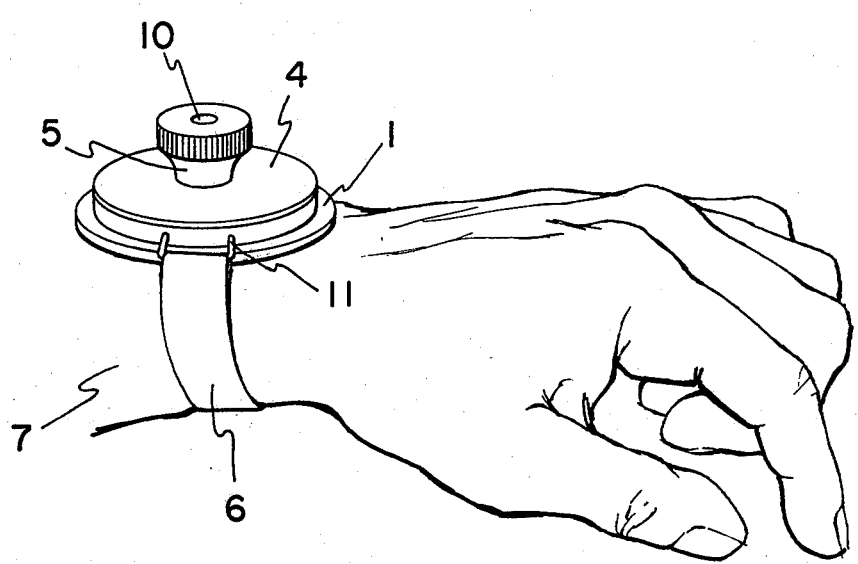
FIG. 1 illustrates a preferred form of the sweat collection capsule as applied to a human subject's skin.
Figure 2:
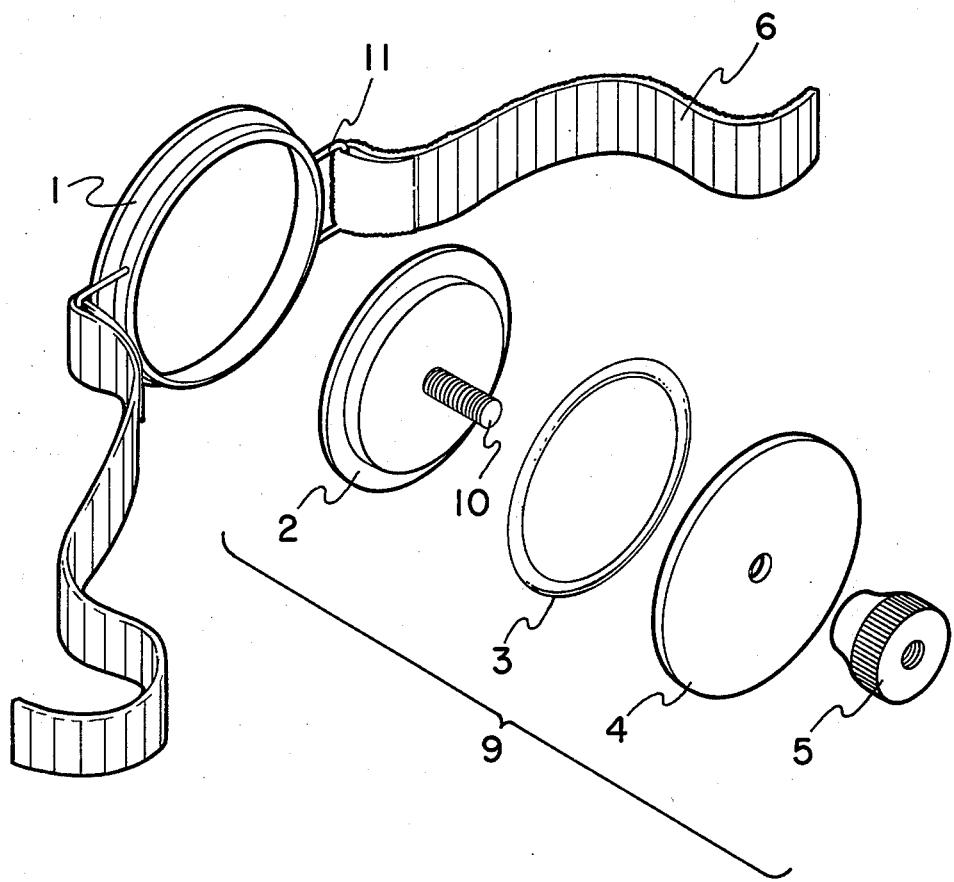
FIG. 2 is an exploded view of a preferred from of the sweat collection capsule.

The preferred embodiment of the sweat collection capsule comprises a frame 1 with a closure 9. The closure 9 is shown in exploded view in FIG. 2, and assembled and secured to the frame 1 in FIG. 3. In the present embodiment of the invention as shown in FIG. 1, frame 1 with closure 9 mounted thereon is held immobile and airtight against the human subject's skin by means of Velcro straps 6 attached to each side of the frame with the aid of staples 11 that are permanently affixed to the frame 1.

Figure 3:
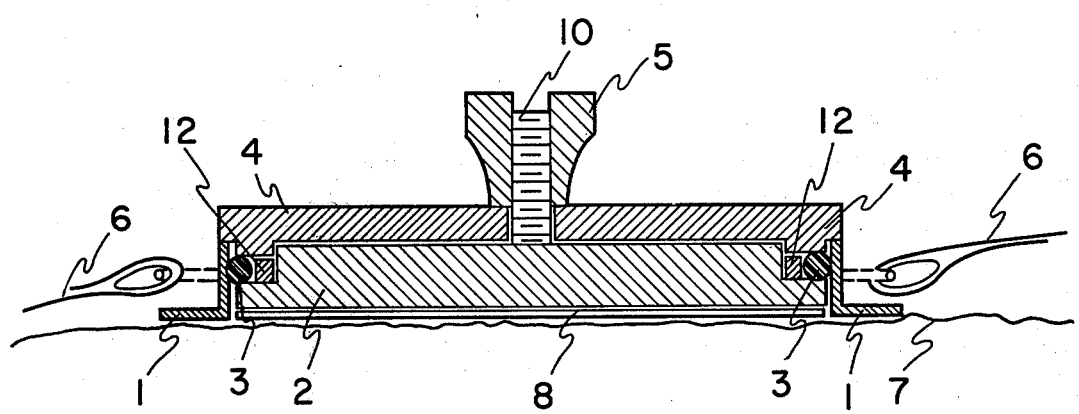
FIG. 3 shows a cross-section of a preferred form of the sweat collection capsule.

In the preferred embodiment depicted in the drawings, the closure 9 comprises a base plate 2, an O-ring 3, a cover plate 4 and a locking device 5. Base plate 2 is provided with a rod 10 protruding perpendicularly from its center. This rod 10 is helically ribbed in the preferred embodiment. O-ring 3 which is placed on the rod side of the base plate is resilent in nature and may be made of rubber or other elastomeric material. Centrally perforated cover plate 4 is then placed on top of the base plate and the O-ring. Locking device 5, which is the preferred embodiment comprising an internal screw, is tightened upon the rod 10 of base plate 2 as illustrated in FIG. 3. The tightening of the locking device 5 causes the cover plate 4 and the base plate 2 to be forced together. The pressure of the cover plate 4 and the base plate 2 on the sides of the O-ring 3 causes the O-ring to extend beyond the base plate and engage the frame in an airtight manner. It may also be desirable to provide an adjusting band 12, as shown in FIG. 3, to occupy the space between the surface of the base plate and the O-ring so that when pressure is exerted as described above the O-ring may only extrude in the direction of the frame.

Frame 1 and closure 9 when assembled provide a cavity to hold the absorbent material 8 that is the means for absorbing the sweat from the skin. Low-electrolyte Whatman No. 541 filter paper is a preferred material for this purpose as it does not interfere with analysis of the various sweat components.

The sweat collection capsule allows for recovery of the absorbent material by removal of the closure while the frame is secured next to the skin rather than by displacement of the entire capsule. The usefulness of a device comprising such a removable frame and immobilized frame may be illustrated as follows. The removable closure characteristic may be useful when one wishes to collect the sweat generated by the skin over an extended period of time. It provides a means for regular removal and replacement of the sweat absorbing material as it reaches saturation. Further, when it is desirable to measure the number of sweat glands which produced the quantity of sweat collected, the closure may be removed while the frame remains in place on the skin clearly defining the area of skin from which the sweat was collected. The number of active sweat glands within that area may then be counted, for example, by painting the skin with tincture of iodine and the placing of a piece of paper with high starch content over area. The sweat produced by active sweat glands will cause a reaction between the iodine and starch leaving purple spots in the paper opposite each sweat gland.

Having described this invention in terms of the embodiments shown in the drawings, it remains understood that the invention is not limited by any of the details of description unless otherwise specified, but rather is to be construed broadly within the spirit and the scope of the following claims.

What is claimed is:

1. A capsule for collecting sweat from the skin of a human subject, which comprises:
   (a) a frame;
   (b) a removable closure adapted to mount on the frame and which, when mounted, leaves a cavity on one side of the frame; said closure comprising (1) a circular base plate adapted to fit within the frame and having a rod protruding perpendicularly from its center; (2) an O-ring for placement on the rod side of the base plate; (3) a cover plate for placement on top of the O-ring and the base place, said cover plate being centrally perforated to accommodate the rod of the base plate; and (4) a locking device operable to engage the rod of the base plate in such a way as to cause the O-ring to expand beyond the perimeter of the base plate and push against the frame in airtight cooperation;

(c) means for absorbing sweat, located within said cavity; and (d) means for attaching the frame to the skin in an immobile and airtight manner.

2. The capsule of claim 1 wherein the rod of the base plate is a helically ribbed cylinder.

3. The capsule of claim 2 wherein the locking device comprises an internal screw.

4. The capsule of claim 1 wherein the cover plate has a perimeter larger than the inner boundary of the frame.

* * * * *